(12) United States Patent
Songer

(10) Patent No.: US 10,485,599 B2
(45) Date of Patent: Nov. 26, 2019

(54) SURGICAL CABLE PASSER INSTRUMENT AND METHODS

(71) Applicant: Matthew Songer, Marquette, MI (US)

(72) Inventor: Matthew Songer, Marquette, MI (US)

(*) Notice: Subject to any disclaimer, the term of this patent is extended or adjusted under 35 U.S.C. 154(b) by 0 days.

(21) Appl. No.: 15/833,750

(22) Filed: Dec. 6, 2017

(65) Prior Publication Data

US 2018/0153603 A1 Jun. 7, 2018

Related U.S. Application Data

(60) Provisional application No. 62/430,892, filed on Dec. 6, 2016.

(51) Int. Cl.

| | | |
|---|---|---|
| *A61B 17/88* | (2006.01) |
| *A61B 90/00* | (2016.01) |
| *A61B 17/00* | (2006.01) |
| *A61B 17/90* | (2006.01) |
| *A61B 17/82* | (2006.01) |

(52) U.S. Cl.
CPC ........ *A61B 17/8861* (2013.01); *A61B 17/82* (2013.01); *A61B 2017/00477* (2013.01); *A61B 2017/90* (2013.01); *A61B 2090/034* (2016.02)

(58) Field of Classification Search
CPC .... A61B 17/82; A61B 17/8861; A61B 17/842
See application file for complete search history.

(56) References Cited

U.S. PATENT DOCUMENTS

| | | | | |
|---|---|---|---|---|
| 4,312,337 A * | 1/1982 | Donohue | A61B 17/1796 |
| | | | 606/103 |
| 5,071,428 A * | 12/1991 | Chin | A61N 1/0587 |
| | | | 606/184 |
| 6,086,596 A * | 7/2000 | Durham | A61B 17/8861 |
| | | | 606/103 |
| 6,423,080 B1 * | 7/2002 | Gellman | A61B 17/00234 |
| | | | 606/148 |
| 6,616,667 B1 * | 9/2003 | Steiger | A61B 17/8861 |
| | | | 606/103 |
| 7,871,424 B2 * | 1/2011 | Abdelgany | A61B 17/7083 |
| | | | 606/103 |
| 9,545,260 B2 * | 1/2017 | Russi | A61B 17/151 |
| 10,080,584 B2 * | 9/2018 | Miller | A61B 17/3403 |
| 2006/0293691 A1 * | 12/2006 | Mitra | A61B 17/8861 |
| | | | 606/103 |

(Continued)

*Primary Examiner* — Nicholas J Plionis
*Assistant Examiner* — Steven J Cotroneo
(74) *Attorney, Agent, or Firm* — Device Patent LLC

(57) ABSTRACT

Surgical cable passer instruments and methods for passing surgical cable around a bone through a surgical incision are disclosed. First and second handle tube portions comprise respective cable guide tubes and handle extensions. A proximal portion of the cable guide tube portions is fixed to a distal portion of the respective handle extension. Each handle tube portions comprise a cannula extending between a near port at a proximal end and a far port at a distal end for passage of surgical cable therebetween. Arc segments of a first cable guide tube and a second cable guide tube define a bone aperture therebetween for passing around a bone. A releasable hinge portion joins a first handle tube portion and a second handle tube portion at distal ends of a first and second handle extension.

20 Claims, 12 Drawing Sheets

(56) References Cited

U.S. PATENT DOCUMENTS

| | | | | |
|---|---|---|---|---|
| 2007/0043377 | A1* | 2/2007 | Fernandez | A61B 17/82 606/103 |
| 2008/0208205 | A1* | 8/2008 | Kraemer | A61B 17/82 606/103 |
| 2008/0243132 | A1* | 10/2008 | Tipirneni | A61B 17/742 606/102 |
| 2009/0171402 | A1* | 7/2009 | Dell'Oca | A61B 17/8861 606/86 R |
| 2009/0306668 | A1* | 12/2009 | Dell'Oca | A61B 17/82 606/74 |
| 2010/0274074 | A1* | 10/2010 | Khamis | A61B 17/00234 600/37 |
| 2011/0166574 | A1* | 7/2011 | Hsu | A61B 17/1796 606/74 |
| 2013/0060261 | A1* | 3/2013 | Ostrovsky | A61B 17/0469 606/139 |

* cited by examiner

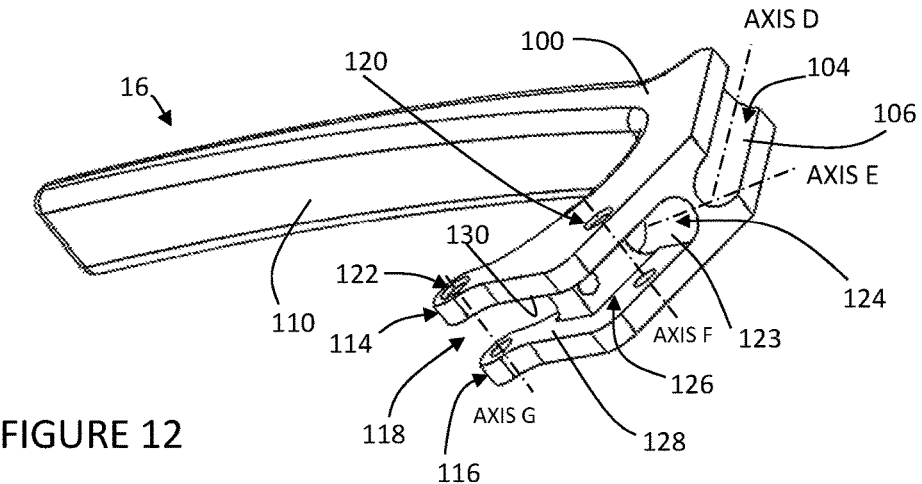
FIGURE 12
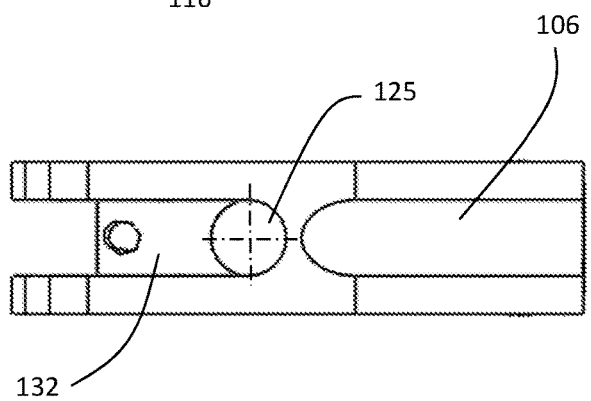
FIGURE 13
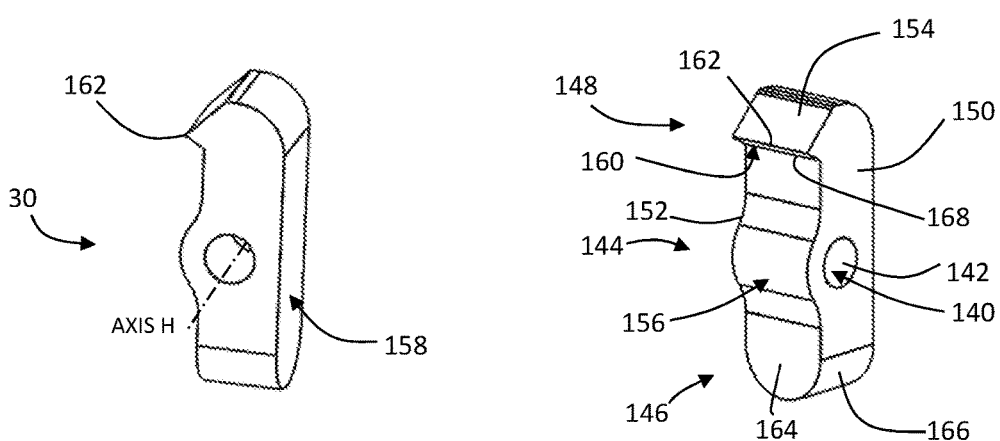
FIGURE 14
FIGURE 15

SURGICAL CABLE PASSER INSTRUMENT AND METHODS

CROSS REFERENCE TO RELATED APPLICATIONS

This application claims priority to Provisional Patent Application No. 62/430,892 filed Dec. 6, 2016, the entire disclosure of which is hereby incorporated by reference and relied upon.

BACKGROUND OF THE INVENTION

Field of the Invention. The invention relates generally to instruments utilized in orthopedic surgery, and more particularly to instruments used in surgery for the passage of surgical cable around bones and methods thereof.

Surgical cable is often used by surgeons as a cerclage to support and repair fractured bones. Once fully looped around the bone, tensioned, and fixed using a crimp or other clamping the device, the cable cerclage works very effectively for bone repair. It is of course always a goal to minimize tissue damage during a surgical procedure and therefore minimize incision size which can make looping of surgical cable around a bone through a small incision very tedious for the surgeon.

Cable passers in the prior art are often difficult to insert and remove from an incision and typically comprise a shape that passes a surgical cable only partially around a bone. The free end of the cable can be difficult to pass through the soft tissues and difficult to locate within an incision. What is needed is a cable passer which has a small insertion and removal profile and provides a completely enclosed surgical cable travel path both in and out of an incision free from binding of soft tissue.

This mating relationship prevents interposing soft tissue between the tip, engages the opposing tips, and facilitates the smooth passage of surgical cable through the cannulas 53 of each cable guide tube and across male end 35 and female end 37. For this reason, it is preferred that surgical cable is fed through the corresponding guide tube having the male end 35 first since the flared taper 41 will act like a funnel to guide a surgical cable into a far port 58 without binding. The cable however may be fed in an opposing direction if needed with generally acceptable results. Also, first cable guide tube 12 and second cable guide tube 14 may be paired with either first handle extension 16 and second handle extension 18 during assembly.

SUMMARY OF THE INVENTION

The present invention comprises specialized surgical instruments and methods of use thereof.

In one form, a surgical instrument is in the form of a surgical cable passer.

In one form, a surgical cable passer comprises a first handle tube portion and a second handle tube portion.

In one form, a first handle tube portion comprises a first cable guide tube and a first handle extension.

In one form, a second handle tube portion comprises a second cable guide tube and a second handle extension.

In one form, a surgical cable passer comprises; a first cable guide tube and an opposing second cable guide tube, a first handle extension and an opposing second handle extension, and a releasable pivot portion.

In one form, a first and second cable guide tube comprises a cannulated rod body.

In one form, a first and a second cable guide tube comprises an entry segment at a proximal end, an arc segment at a distal end, and an intermediate segment between an entry segment and arc segment.

In one form, a second cable guide tube is generally identical to a first cable guide tube.

In one form, a second cable guide tube is dimensionally different than a first cable guide tube.

In one form, the entire central axis of a first or a second or both a first and a second guide tube resides in a single plane.

In one form, a cannula extends the entire length of a first and second cable guide tube from a proximal end to a distal end.

In one form, a cannula of a first and a second cable guide tube is defined by an inner surface.

In one form, a near port provides entry through a near face into a cannula on a proximal end of a first or second cable guide tube.

In one form, a far port provides entry through a far face into a cannula on a distal end of a first or second cable guide tube.

In one form, a proximal end of an entry segment of a cable guide tube is angled away from a central axis of the instrument.

In one form, an inner surface defines a cannula extending the length of one or more cable guide tubes.

In one form, intermediate segments on a first and a second cable guide tube are generally parallel in an operational configuration.

In one form, a proximal bend forms a smooth transition in a cannula between an entry segment and an intermediate segment of one or more of a first cable guide tube and a second cable guide tube.

In one form, a distal bend forms a smooth transition in a cannula between an intermediate segment and an arc segment of one or more of a first cable guide tube and a second cable guide tube.

In one form, an arc segment of one or more of a first and a second cable guide tube comprises a radius sufficient to fit around the outer diameter of a human bone.

In one form, a central axis of a first and second cable guide tube at their distal ends align and far faces of each cable guide tube are directly opposed providing for the continuous passage of a surgical cable though a first cable guide tube and through a second cable guide tube.

In one form, a second handle extension comprises a second handle body.

In one form, a second handle body comprises a second handle end at the proximal end of a second handle extension.

In one form, a second handle body comprises an opposing second press face and under face formed thereon.

In one form, a second handle body comprises a press face for distributing forces from a user's hand.

In one form, a second handle body comprises an under face defining the underside of a second handle extension.

In one form, a pivot boss extends from a distal end of a second handle body.

In one form, a pivot boss is partially defined by opposed first and second lateral faces.

In one form, a pivot boss comprises a restraint cavity.

In one form, a restraint cavity is defined by opposed first restraint face and second restraint face separated by a restraint elbow.

In one form, a pivot boss comprises a pivot cup on a proximal end of the pivot boss. The pivot cup is defined by a curved pivot face for articulation against a pivot pin.

In one form, a pivot boss comprises a sole facing generally medial in the instrument.

In one form, at a distal end of a second handle body is a second channel face defining a second tube channel for seating of a second cable guide tube.

In one form, the second channel face comprises a central axis angled from a medial axis of the instrument.

In one form, a first handle extension comprises a first handle body.

In one form, a first handle body comprises a first handle end at the proximal end of the first handle extension.

In one form, a first handle body comprises opposing first press face and under face formed thereon.

In one form, a first handle body comprises a first press face for distributing forces from a user's hand.

In one form, a first handle body comprises an under face defining an underside of a first handle extension.

In one form, a pivot claw extends from a distal end of the first handle body.

In one form, a pivot claw includes a first pivot finger and a second pivot finger.

In one form, a pivot cavity spaces a first pivot finger and a second pivot finger.

In one form, a pivot cavity is defined by a first cavity face and an opposing second cavity face.

In one form, a pivot cavity resides between a first pivot finger and a second pivot finger.

In one form, a first handle body comprises a rocker cavity defined by a first cavity face and an opposed second cavity face at a distal end of a first handle body.

In one form, a spring cavity extends proximally from a rocker cavity and is defined by a spring face and a spring base at a terminal end of the spring cavity.

In one form, a base wall spans between a first cavity face and a second cavity face providing support to a pivot claw.

In one form, a rocker is used to releasably secure a first handle extension to a second handle extension.

In one form, a rocker cavity is sized to pivotably house a rocker.

In one form, a rocker hole extends across a first and second cavity wall for seating a rocker pin.

In one form, a rocker pin is seated within a pair of spaced rocker holes and rocker aperture of a rocker to provide for pivoting motion between a rocker and a first handle body.

In one form, a handle hole extends between a first pivot finger and a second pivot finger and through a first and second cavity face for seating a handle pin.

In one form, a pivot boss of a second handle portion is housed within a pivot cavity of a first handle portion in an operational configuration.

In one form, a pivot cup of a second handle extension pivots about a handle pin in a first handle extension in an operational configuration.

In one form, a pivot cup of a second handle extension is separated from a handle pin in a first handle extension in a pre-operational configuration.

In one form, a restraint tip is obstructed from release from a tooth on a rocker in a locked configuration.

In one form, a restraint tip is un-obstructed from release from a tooth on a rocker during an un-locked configuration.

In one form, at a distal end of a first handle portion is a first channel face defining a first tube channel for seating of a first cable guide tube.

In one form, a first channel face comprises a central axis angled from a medial axis of the instrument.

In one form, a releasable restraint is used to hold a first handle extension to a second handle extension.

In one form, a releasable restraint comprises a rocker.

In one form, a rocker comprises a pivot portion, a spring lever portion, and tooth portion.

In one form, a rocker comprises opposing first and second pivot walls.

In one form, a rocker pivot portion comprises a rocker aperture extending through the opposed first and second pivot walls.

In one form, a rocker pivot portion comprises a belly wall.

In one form, a rocker pivot portion comprises a back wall.

In one form, a rocker pivot portion comprises a tooth extending from a belly wall of a tooth portion.

In one form, the tooth comprises a linear lip.

In one form, the tooth comprises a sloped entry face.

In one form, the tooth comprises a sloped chin.

In one form, the belly wall comprises a spring pad at a spring lever portion on a belly wall of a rocker.

In one form, a biasing element is positioned between a spring pad on a rocker and a spring base on a first handle extension.

In one form, as a consequence of a biasing element therebetween, a spring pad and spring base are pushed apart causing a tooth portion of a rocker to rotate.

In one form, a rocker is pivotably held within a rocker cavity using a rocker pin extending through one or more rocker holes of a first handle extension and a rocker aperture of a rocker.

In one form, a biasing element is in the form of a spring.

In one form, the biasing element causes a tooth on a rocker to releasably engage a restraint tip on a pivot boss portion of a second handle extension.

In one form, an outer surface of a first cable guide tube is fixed to a first channel face of a first tube channel of a first handle extension to form a first handle tube portion.

In one form, an outer surface of a second cable guide tube is fixed to a second channel face of a second tube channel of a second handle extension to form a second handle tube portion.

In one form, a weld is used to secure an outer surface of a first cable guide tube to a first channel face of a first handle extension.

In one form, a weld is used to secure an outer surface of a second cable guide tube to a second channel face of a second handle extension.

In one form, a surgical cable passer has a profile that is generally aligned in a single place.

In one form, a method of using a surgical cable passer instrument comprises the following steps. Grasping a first handle body with one hand and a second handle body with a second hand. Applying a separation force on the handle bodies towards a central instrument axis to cause a restraint tip on a second handle extension to release from under a biased tooth of a rocker portion. Extending a cable guide tube of a first handle tube portion into an incision and looping an arc segment of the first cable guide tube around a targeted bone segment. Extending a cable guide tube of a second handle tube portion into the incision and looping an arc segment of a second cable guide tube around a targeted bone segment from an opposing side of the bone. Aligning central planes for the first cable guide tube and second cable guide tube. Moving a pivot cup of a second handle extension over a handle pin portion secured in a first handle extension whereby the first handle tube portion articulates with a second handle tube portion. Separating a first handle extension from a second handle extension causing a restraint tip to engage then move past a biased tooth causing the first handle extension and second handle extension to be pivotably locked together and until far faces on opposing cable guide tubes are adjacent and cannulas between a first cable guide tube and a second cable guide tube are continuous. Aligning the tip of a surgical cable with a near port of one of the cable guide tubes and advancing the cable through the cannula and exiting the cable from the near port of the opposing cable guide tube. Applying forces on the first and second handle extension to cause the first and second cable guide tubes to move away from each other while concurrently causing a restraint tip of a second handle extension to slide against and be released from the tooth of a biased rocker. Separating the pivot cup of a second handle extension from a handle pin portion of a first handle extension. Then retracting a first handle tube portion and a second handle tube portion from the incision while leaving the surgical cable looped around the bone. Then proceeding to tighten and secure the surgical cable using one or more of a cable tensioner, a cable retensioner, and a crimp or other cable locking device.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 12 depicts a distal end perspective view of a first handle extension according to one or more embodiments shown and described herein;

FIG. 13 depicts a distal end view of a first handle extension according to one or more embodiments shown and described herein;

FIG. 14 depicts a side perspective view of a rocker according to one or more embodiments shown and described herein;

FIG. 15 depicts a proximal perspective view of a rocker according to one or more embodiments shown and described herein;

DETAILED DESCRIPTION OF SELECTED EMBODIMENTS OF THE INVENTION

Selected embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
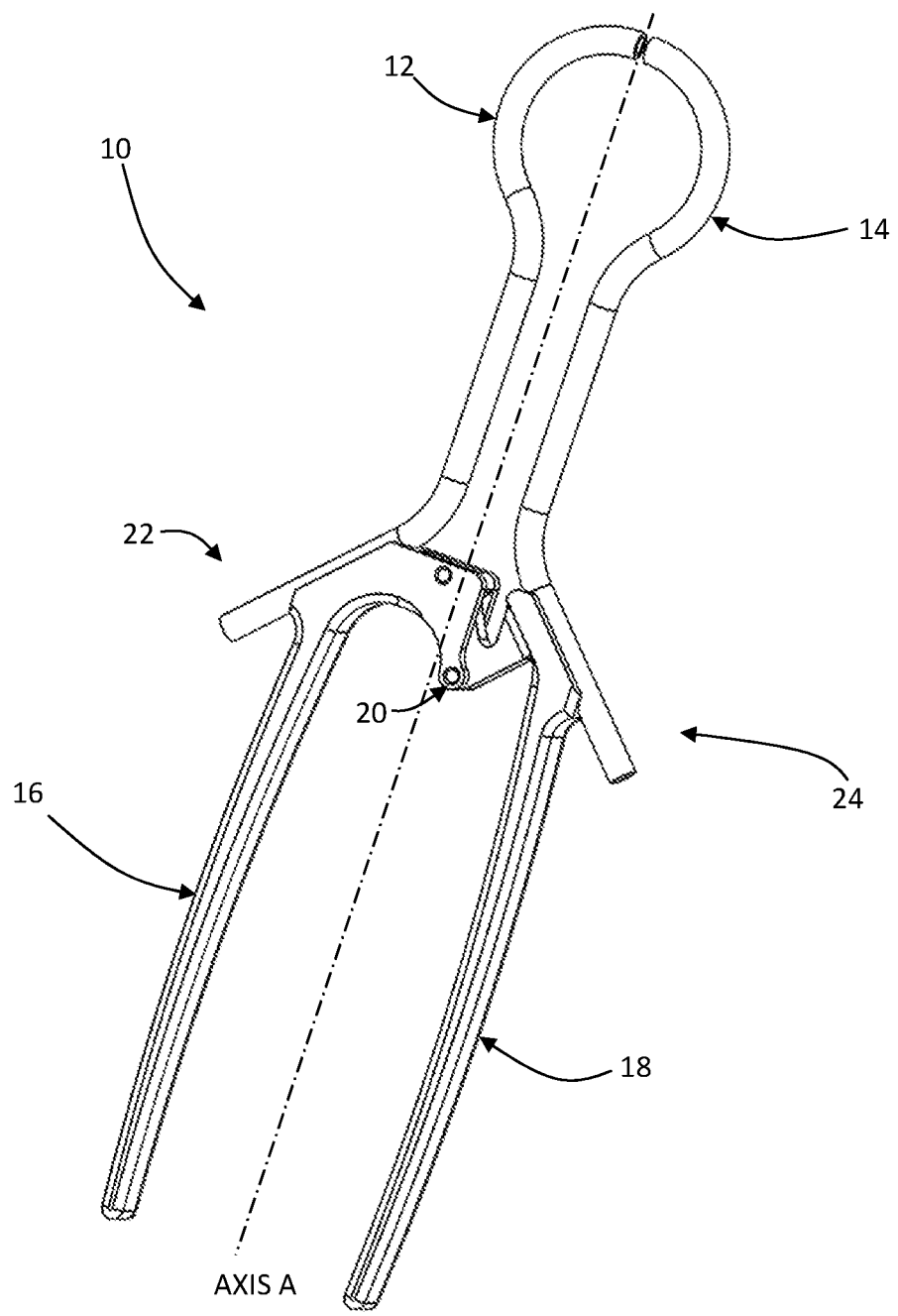
FIG. 1 depicts a perspective view of a cable passer according to one or more embodiments shown and described herein.

FIG. 1 illustrates a preferred embodiment of the invention in the form of a surgical cable passer 10. FIG. 2 provides an exploded view of the same instrument. In this embodiment a surgical cable passer comprises; a first cable guide tube 12 and an opposing second cable guide tube 14, a first handle extension 16 and an opposing second handle extension 18, and a releasable hinge portion 20.

Figure 3:
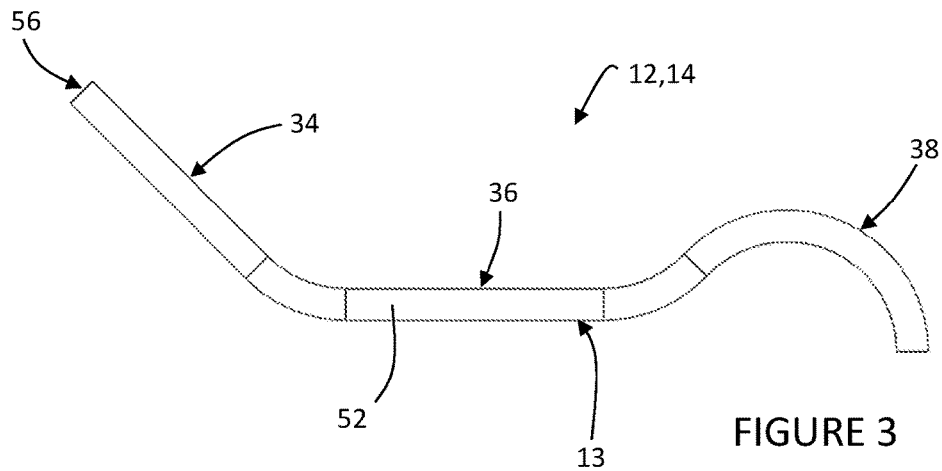
FIG. 3 depicts a front view of a cable guide tube according to one or more embodiments shown and described herein.
Figure 4:
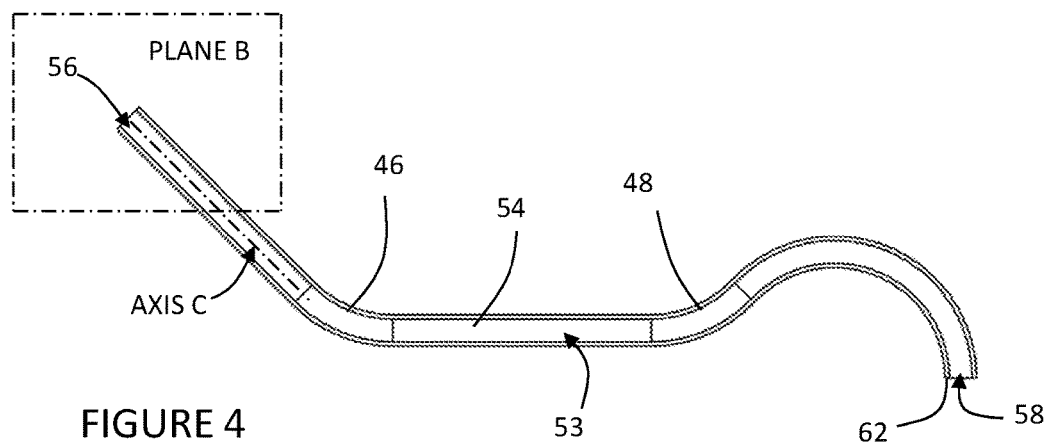
FIG. 4 depicts a cross-sectional view of a cable guide tube along plane B according to one or more embodiments shown and described herein.
Figure 5:
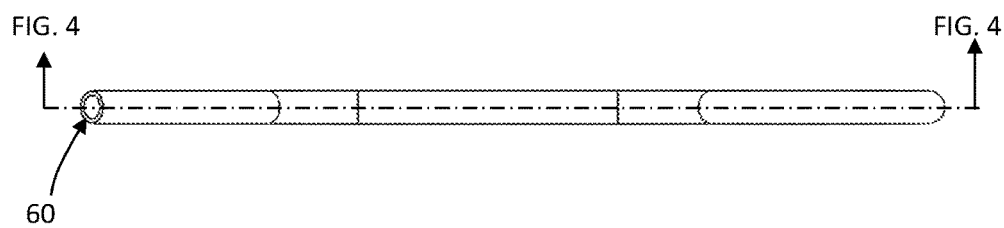
FIG. 5 depicts a side view of a cable guide tube according to one or more embodiments shown and described herein.

A first cable guide tube 12 and second cable guide tube 14 comprise a cannulated rod body 13 as illustrated in FIG. 3-5. FIG. 4 is a cross-sectional view along plane B. First and second cable guide tube 12,14 comprise an entry segment 34 at a proximal end, an arc segment 38 at a distal end, and an intermediate segment 36 between an entry segment 34 and arc segment 38. Distal bend 48 separates arc segment 38 and intermediate segment 36.

In this embodiment, a second cable guide tube 14 is generally identical to a first cable guide tube 12, however in other embodiments; a second cable guide tube 14 is dimensionally different or comprises an alternative shape than a first cable guide tube 12.

Figure 2A:
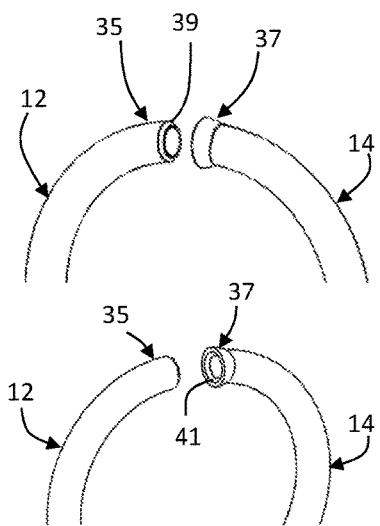
FIG. 2A depicts two partial perspective views of male and female ends of opposing guide tubes of a cable passer according to one or more embodiments shown and described herein.
Figure 2:
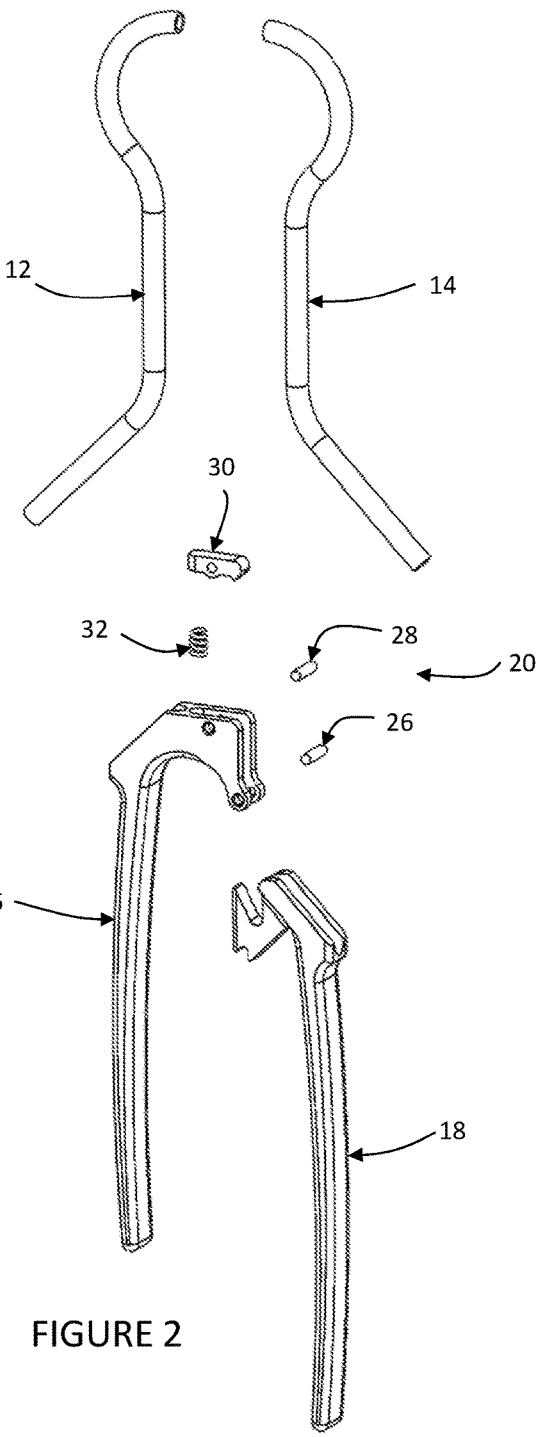
FIG. 2 depicts an exploded perspective view of the cable passer of FIG. 1 according to one or more embodiments shown and described herein.

FIG. 2A illustrates two partial perspective views of a preferred embodiment of a modified first cable guide tube 12 and a second cable guide tube 14 wherein a far face 62 at a far port 58 of each cable guide tube 12, 14 is modified to have a coupling relationship. Best illustrated in a lower figure of FIG. 2A, second cable guide tube 14 comprises a female end 37 characterized by a flare taper 41. Best illustrated in an upper figure of FIG. 2A, first cable guide tube 12 comprises a male end 35 characterized by a cone taper 39. Cone taper 39 and flare taper 41 are configured to mate together when first and second handle extensions 16,18 are moved to cause male end 35 and female end 37 to abut. This mating relationship prevents interposing soft tissue between the tip, engages the opposing tips, and facilitates the smooth passage of surgical cable through the cannulas 53 of each cable guide tube and across male end 35 and female end 37. For this reason, it is preferred that surgical cable is fed through the corresponding guide tube having the male end 35 first since the flared taper 41 will act like a funnel to guide a surgical cable into a far port 58 without binding. The cable however may be fed in an opposing direction if needed with generally acceptable results. Also, first cable guide tube 12 and second cable guide tube 14 may be paired with either first handle extension 16 and second handle extension 18 during assembly.

In this embodiment, a central axis of a first or a second or both a first and a second guide tube resides in a single plane as illustrated by plane B in FIG. 4. As illustrated, a cannula 53 extends the entire length of a first and second cable guide tube 12,14 from a proximal end to a distal end and is defined by an inner surface 54. A near port 56 provides entry through a near face 60 into a cannula 53 on a proximal end of a first or second cable guide tube 12, 14. A far port 58 provides entry through a far face 62 into a cannula 53 on a distal end of a first or second cable guide tube 12,14. In this embodiment, an entry segment 34 along axis C is angled away from a central axis A of the instrument as illustrated in FIG. 1.

Further in this embodiment, an inner face 54 defines a cannula 53 extending the length of one or more cable guide tubes 12, 14. Intermediate segments 36 on a first and a second cable guide tube 12,14 are parallel although in alternative embodiments they are non-parallel. A proximal bend 46 forms a smooth transition in a cannula 53 between an entry segment 34 and an intermediate segment 36 of one or more of a first cable guide tube 12 and a second cable guide tube 14. A distal bend 48 forms a smooth transition in a cannula 53 between an intermediate segment 36 and an arc segment 38 of one or more of a first cable guide tube 12 and a second cable guide tube 14. An arc segment 38 of one or more of a first and a second cable guide tube 12,14 comprises a radius sufficient to fit around a long diameter of a human bone. Alternatively, arc segment 38 may be curved but not have a defined radius.

Figure 23:
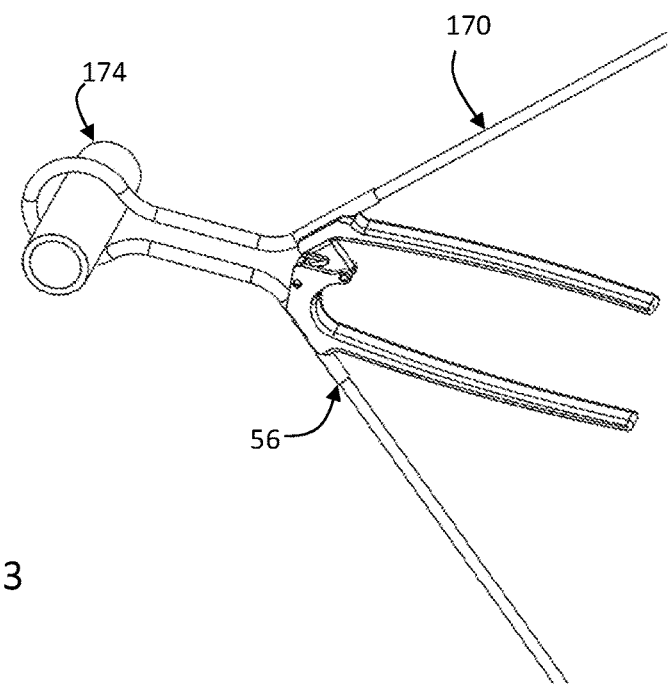
FIG. 23 depicts a perspective view of a cable passer in use with a cable advanced through a cannula of a first cable guide tube and exiting a cannula of a second cable guide tube according to one or more embodiments shown and described herein.

In this embodiment, and in an operable configuration, the central axis of a first and second cable guide tube 12,14 at their distal ends align and far faces 62 for each opposed guide tube 12,14 are directly opposed providing for the continuous passage of a surgical cable though a first cable guide tube 12 and through a second cable guide tube 14 as illustrated in FIG. 23.

Figure 6:
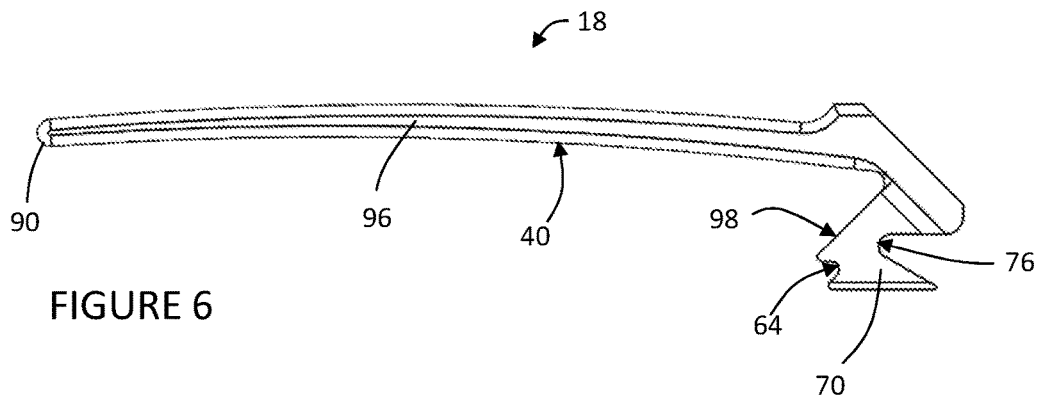
FIG. 6 depicts a front view of a second handle extension of a cable passer according to one or more embodiments shown and described herein.

In this embodiment illustrated in FIG. 6, a second handle extension 18 comprises an elongate second handle body 40. A second handle end 90 is positioned at a proximal end of the second handle extension 18. A second handle body 40 comprises opposed side surfaces 96 thereon. It also includes a second press face 92 for distributing forces from a user's hand. An under face 94 defines the underside of a second handle extension 18. In preferred forms, both first handle extension 16 and second handle extension 18 are proximally bowed outwardly away from a median axis A of a surgical cable passer instrument 10.

Figure 7:
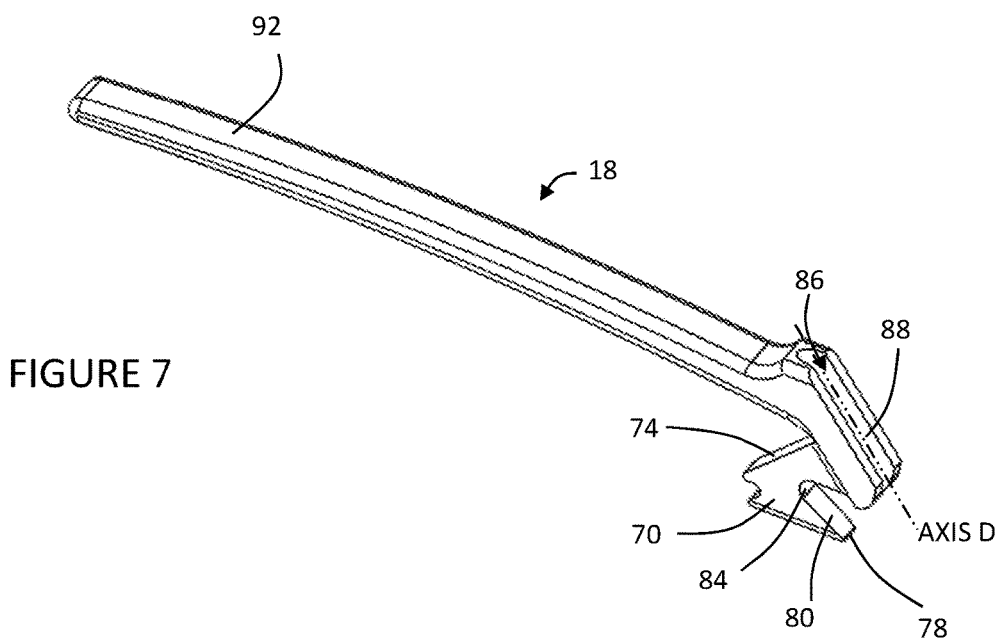
FIG. 7 depicts a lateral side perspective view of a second handle extension according to one or more embodiments shown and described herein.
Figure 8:
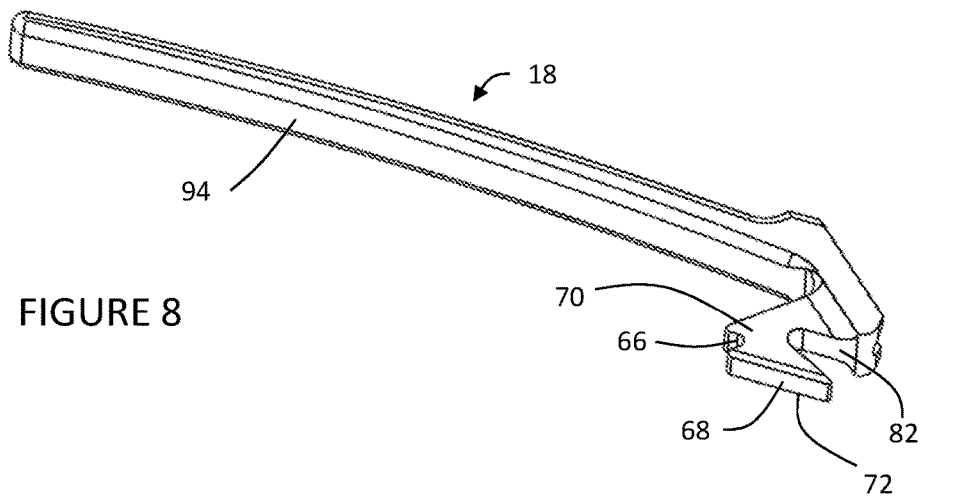
FIG. 8 depicts a medial side perspective view of a second handle extension according to one or more embodiments shown and described herein.
Figure 9:
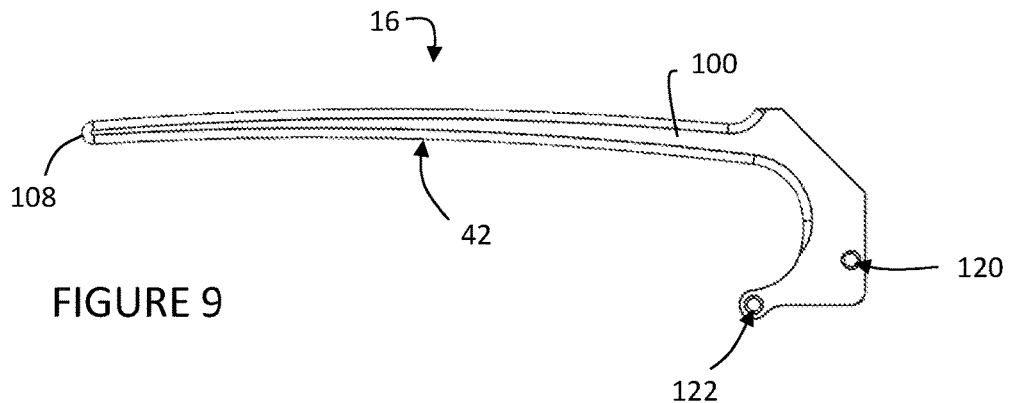
FIG. 9 depicts a front view of a first handle extension according to one or more embodiments shown and described herein.
Figure 10:
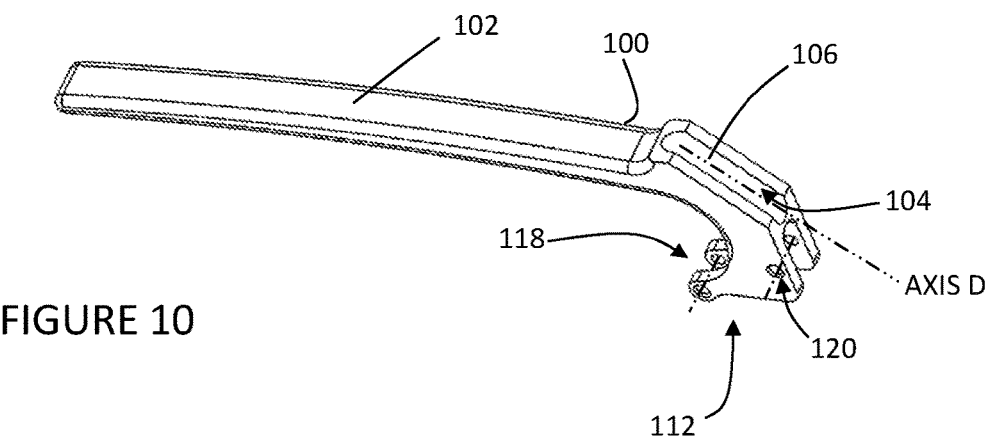
FIG. 10 depicts a lateral side perspective view of a first handle extension according to one or more embodiments shown and described herein.
Figure 11:
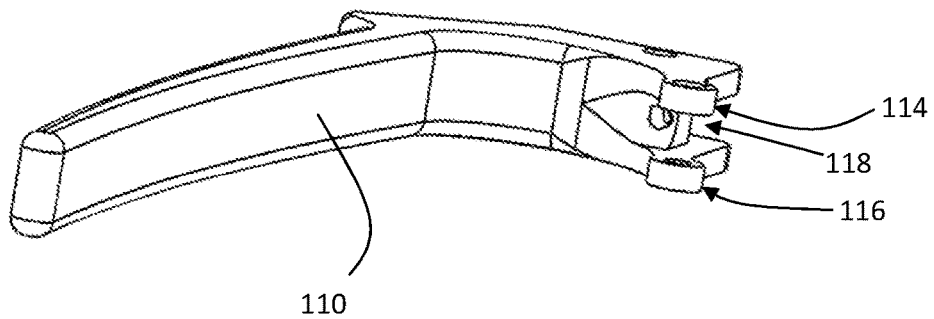
FIG. 11 depicts a medial side perspective view of a first handle extension according to one or more embodiments shown and described herein.

Further illustrated in FIGS. 6-8, a pivot boss 98 extends medially from a distal end of the second handle body 40 and is partially defined by opposed first and second lateral faces 70, 72. In this embodiment, pivot boss 98 comprises a restraint cavity 76 defined by opposed first restraint face 80 and second restraint face 82 separated by a restraint elbow 84. A pivot cup 64 resides on a proximal end of pivot boss 98 and is defined by a curved pivot face 66 for articulation against a pivot pin providing for articulation between a first handle extension 16 and a second handle extension 18. In preferred embodiments, pivot cup 64 is partially open and operable for lateral separation from the pivot pin. Pivot boss 98 comprises a sole 68 facing generally medial in the instrument in an operational configuration. In one form, a pivot boss 98 comprises a back face 74 at a proximal end of the pivot boss and at a distal end of a second handle portion is a second channel face 88 defining a second tube channel 86 for seating of a second cable guide tube 14. A second channel face 88 comprises a central axis-D angled from a medial axis-A of the instrument.

As illustrated in FIGS. 9-13, a first handle extension 16 comprises a first handle body 42. First handle body 42 comprises a first handle end 108 at the proximal end of the first handle extension 16 and opposing side surfaces 100 thereon. A first press face 102 defines a lateral side of first handle body 42 for distributing forces from a user's hand. An under face 110 defines an underside of a first handle extension 16. A pivot claw 112 extends from a distal end of the first handle body 42 which includes a first pivot finger 114 and a second pivot finger 116 spaced in this embodiment by a pivot cavity 118. A pivot cavity 118 is defined by a first cavity face 128 and an opposing second cavity face 130 as illustrated in FIG. 12.

In this embodiment, first handle body 42 comprises a rocker cavity 126 also defined by a first cavity face 128 and an opposed second cavity face 130 at a distal end of a first handle body 42. A spring cavity 124 for housing a spring extends proximally from rocker cavity 126 and is defined by a spring face 123 and a spring base 125 at a terminal end of the spring cavity 124. A base wall 132 spans between a first cavity face 128 and a second cavity face 130 providing support to pivot claw 112.

Figure 18:
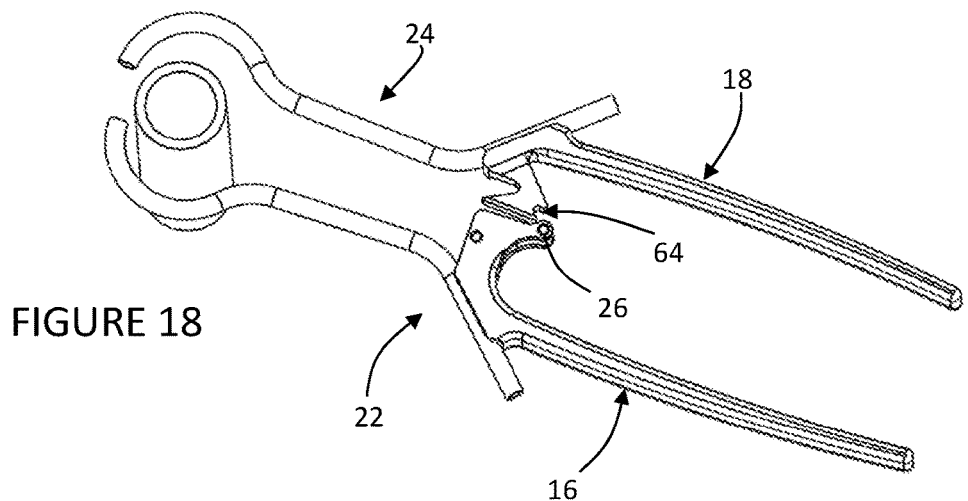
FIG. 18 depicts a perspective view of a first handle tube portion and second handle tube portion of a cable passer being aligned for pivoting engagement according to one or more embodiments shown and described herein.
Figure 19:
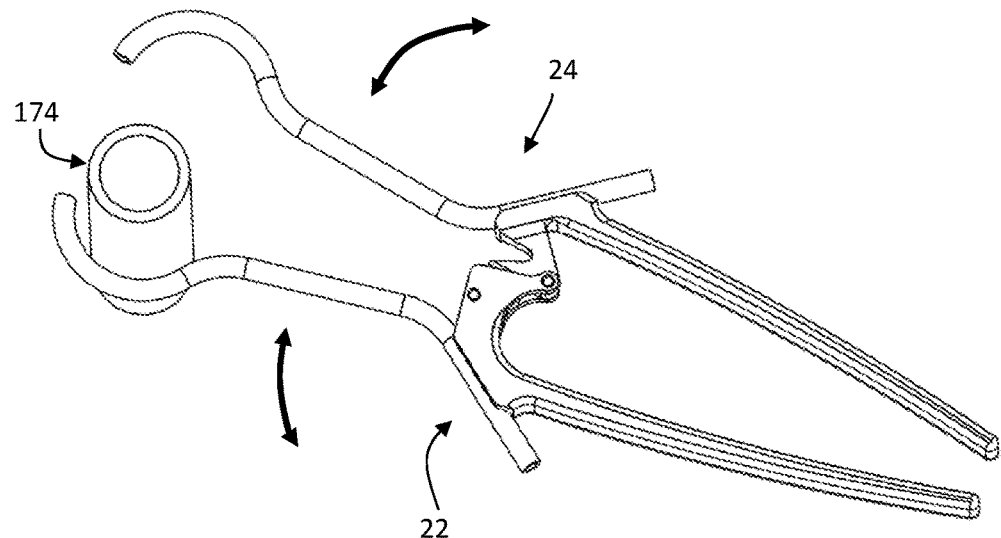
FIG. 19 depicts a perspective view of a first handle tube portion and a second handle tube portion of a cable passer pivotably engaged according to one or more embodiments shown and described herein.

Rocker 30 (FIG. 14,15) is used to releasably secure a first handle extension 16 to a second handle extension 18. Rocker cavity 126 is sized to pivotably house a rocker 30. A rocker hole 120 extends across first and second cavity face 128, 130 for seating a rocker pin 28. Rocker pin 28 extends through a rocker hole 120 and rocker cavity 126 to provide for pivoting motion between a rocker 30 and a first handle body 42. A handle hole 122 extends between a first pivot finger 114 and a second pivot finger 116 and through a first and second cavity face 128,130 for seating a handle pin 26. A pivot boss 98 of a second handle extension 18 is housed within pivot cavity 118 of a first handle extension 16 in an operational configuration. As illustrated in FIG. 18-19, a pivot cup 64 of a second handle extension 18 pivots about a handle pin 26 in a first handle extension 16 in an operational configuration.

At a distal end of first handle extension 16 is a first channel face 106 defining a first tube channel 104 shaped for seating of a first cable guide tube 12. First channel face 106 comprises a central axis angled from a medial axis of the instrument. A releasable hinge portion 20 is used to hold a first handle extension 16 to a second handle extension 18. In a preferred embodiment, a releasable hinge portion 20 comprises a rocker 30. Rocker 30 comprises a pivot portion 144, a spring lever portion 146, and tooth portion 148 (FIG. 14-15). Rocker 30 further comprises opposing first and second pivot walls 150, 152. A rocker pivot portion 144 comprises a rocker aperture 140 extending through opposed first and second pivot walls 150,152. Rocker pivot portion 144 comprises a belly wall 156, a back wall 158, and a tooth extending from a belly wall 156 of a tooth portion 148. Tooth 160 comprises a linear lip 162 that is generally parallel to Axis H with a sloped entry face 154 and a sloped chin 168. Belly wall 156 comprises a spring pad 164 for acting against the end of a spring at a spring lever portion 146 on belly wall 156 of rocker 30. A terminal end of a spring lever portion 146 of a rocker 30 is rounded into a tail 166. A biasing element, such as a spring 32, is positioned between a spring pad 164 on a rocker 30 and a spring base 125 on a first handle extension 16. A biasing element causes spring pad 164 and spring base 125 to be pushed apart causing a tooth portion 148 of a rocker 30 to rotate and interfere with restraint tip 78. In preferred embodiments, the biasing element is in the form of a spring 32.

Rocker 30 is pivotably seated within rocker cavity 126 using a rocker pin 28 extending through one or more rocker holes 120 of a first handle extension 16 and a rocker aperture 140 of a rocker 30. Rocker aperture 140 is defined by channel surface 142. The biasing element causes a tooth 160 to releasably engage a restraint tip 78 on a pivot boss portion of a second handle extension 18.

Further to this embodiment, an outer surface 52 of a first cable guide tube 12 is fixed to a first tube face 106 of a first tube channel 104 of a first handle extension 16 to form a first handle tube portion 22. Outer surface 52 of a second cable guide tube 14 is fixed to a second channel face 88 of a second tube channel 86 of a second handle extension 18 to form a second handle tube portion 24. In each case a weld may be used between outer surface 52 of each guide tube 12, 14 to secure to the respective first and second tube faces 88, 106.

Figure 16A:
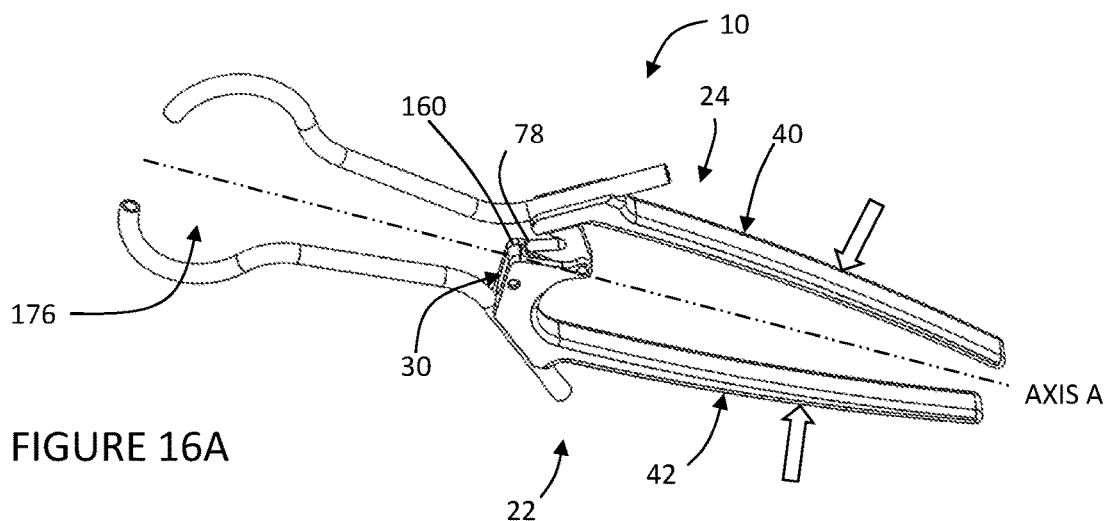
FIG. 16A depicts a perspective view of a cable passer according to one or more embodiments shown and described herein in a configuration leading to separation of a first handle tube portion from a second handle tube portion.
Figure 16:
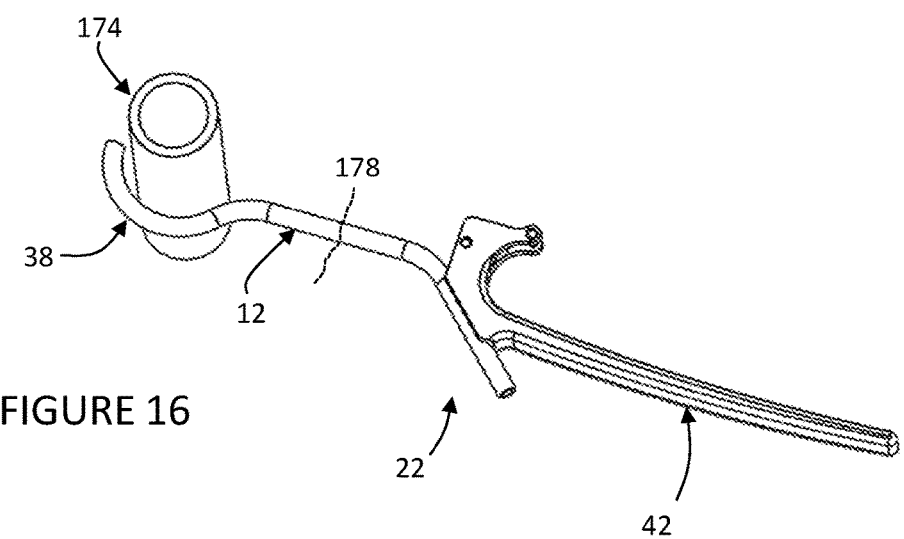
FIG. 16 depicts a perspective view of a first handle tube portion being inserted into an incision and coupling a bone portion according to one or more embodiments shown and described herein.
Figure 17:
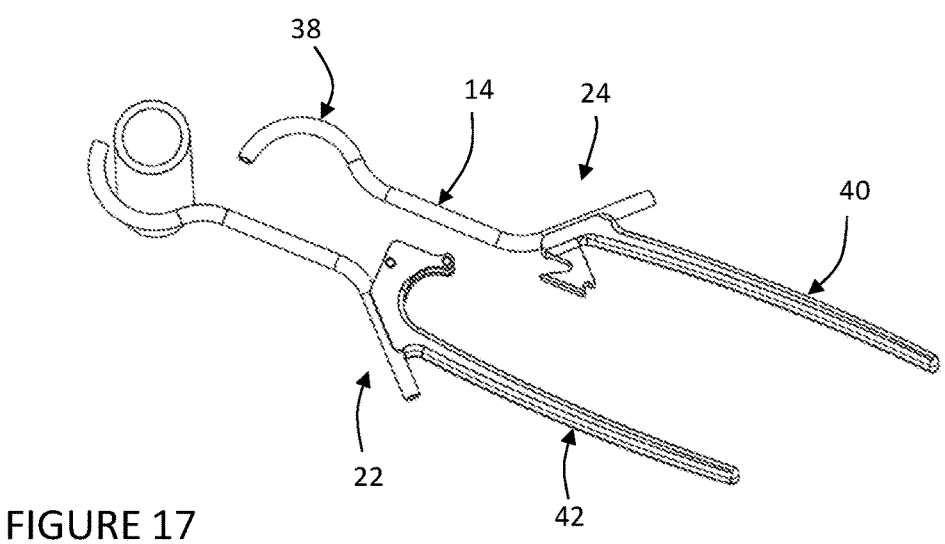
FIG. 17 depicts a perspective view of a second handle tube portion being inserted into an incision in preparation for mating with the first handle tube portion of FIG. 16 according to one or more embodiments shown and described herein.
Figure 20:
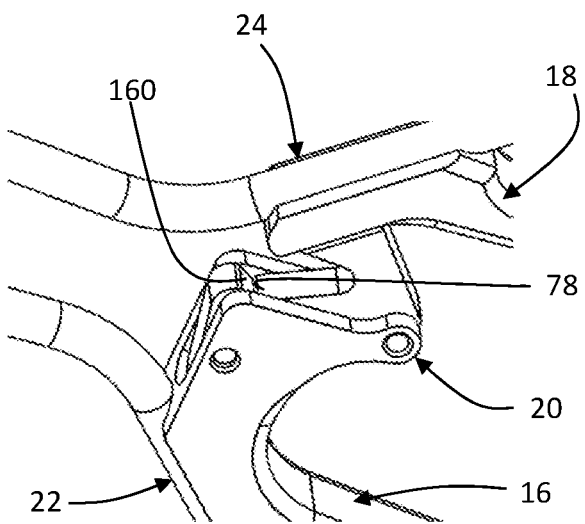
FIG. 20 depicts a partial perspective view of a restraint tip of a second handle extension abutting a tooth on a rocker of a cable passer according to one or more embodiments shown and described herein.
Figure 21:
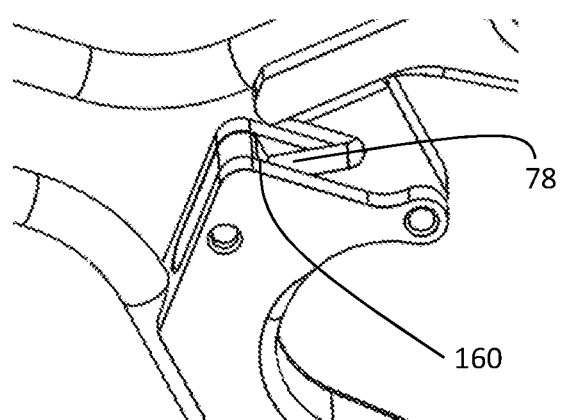
FIG. 21 depicts a partial perspective view of a restraint tip of a second handle extension passed behind a tooth on a rocker of a cable passer according to one or more embodiments shown and described herein.
Figure 22:
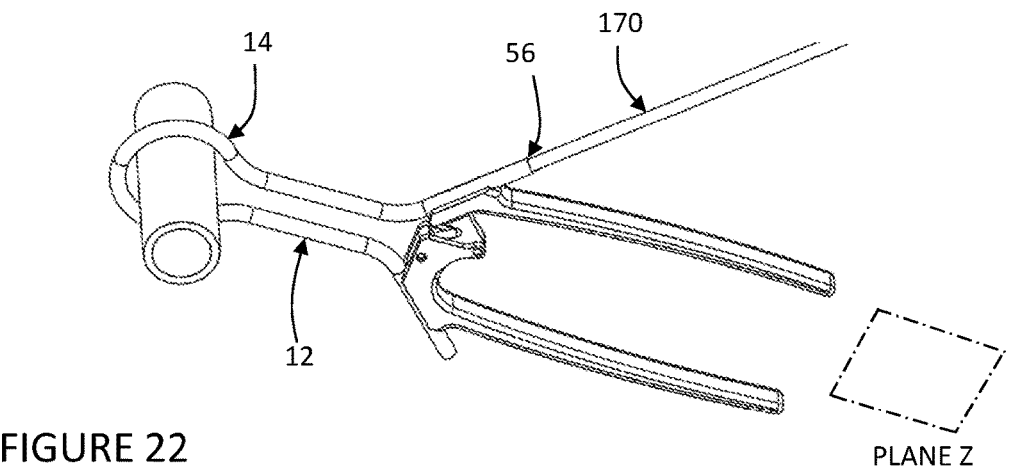
FIG. 22 depicts a perspective view of a cable passer in use wherein a first cable guide tube and a second cable guide tube form a continuous path about a bone and the step of aligning a tip of a surgical cable with a near port of one of the cable guide tubes according to one or more embodiments shown and described herein.
Figure 24:
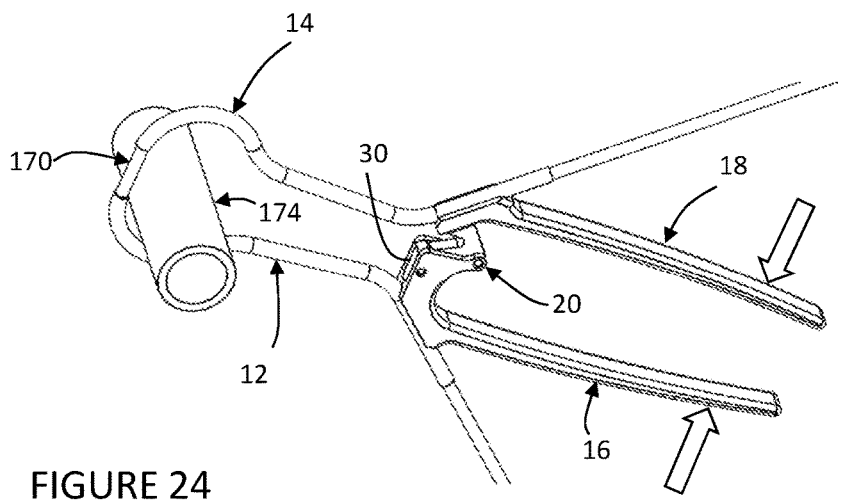
FIG. 24 depicts a perspective view of a cable passer in use wherein applied forces to a first and second handle extension prepare for release of a first handle tube portion from a second handle tube portion according to one or more embodiments shown and described herein.
Figure 25:
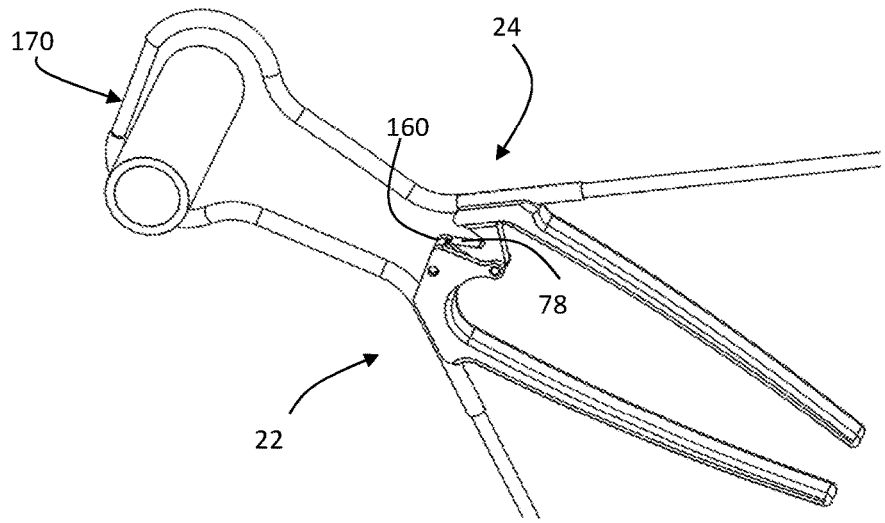
FIG. 25 depicts a perspective view of a cable passer in use wherein a first handle tube portion is released from a second handle tube portion at a releasable hinge portion according to one or more embodiments shown and described herein.
Figure 26:
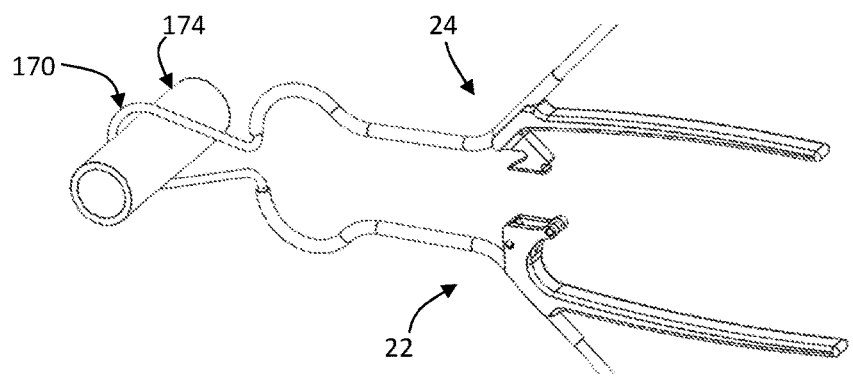
FIG. 26 depicts a perspective view of a cable passer in use wherein a first handle tube portion is separated from a second handle tube portion and beginning to retract the instrument from an incision according to one or more embodiments shown and described herein.
Figure 27:
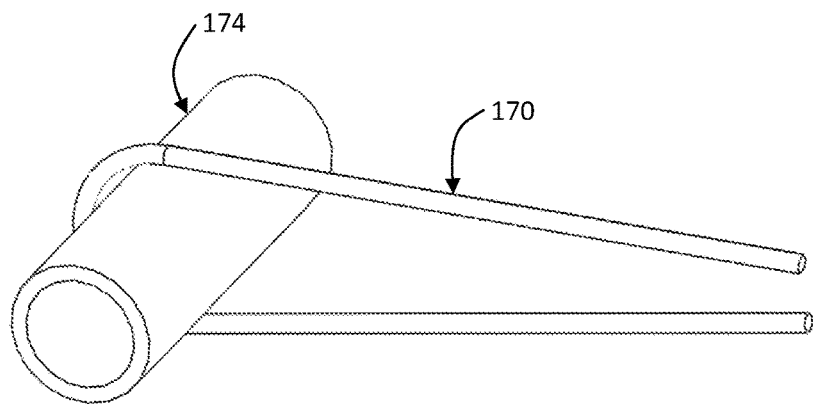
FIG. 27 depicts a perspective view of a surgical cable looped around a bone in preparation for cable tensioning and locking according to one or more embodiments shown and described herein.

In one form, a method of using a surgical cable passer instrument 10 comprises the following steps beginning with the illustration of FIG. 16A. Grasping a first handle body 42 with one hand and a second handle body 40 with a second hand and applying a release force on the handle bodies towards a central instrument axis A to cause a restraint tip 78 on a second handle extension 18 to release from under a biased tooth 160 of a rocker 30 portion leading to separation of first handle tube portion 22 from second handle tube portion 24. Extending a cable guide tube 12 (FIG. 16) of a first handle tube portion 22 into an incision 178 and looping an arc segment 38 of the first cable guide tube 12 around a targeted bone segment (alternatively the procedure could begin by extending a second cable guide tube first followed by a first cable guide tube). Extending a cable guide tube of a second handle tube portion 24 (FIG. 17) into the incision 178 and looping an arc segment 38 of a second cable guide tube 14 around a targeted bone segment 174 from an opposing side of the bone. Aligning central planes for the first cable guide tube 12 and second cable guide tube 14. Moving a pivot cup 64 (FIG. 18) of a second handle extension 18 over a handle pin 26 portion secured in a first handle extension 16 whereby the first handle tube portion 22 articulates with a second handle tube portion 24 (FIG. 19). Separating a first handle extension 16 from a second handle extension 18 (forces applied opposite those in FIG. 16A, forces move away from axis-A) causing a restraint tip 78 to engage (FIG. 20) then move past a biased tooth 160 (FIG. 21) causing first handle extension 16 and second handle extension 18 to be pivotably locked together. With continued movement, far faces 62 on each opposing cable guide tube abut and cannulas 53 between a first cable guide tube 12 and a second cable guide tube 14 are continuous. Aligning the tip of a surgical cable 170 (FIG. 22) with a near port 56 of one of the cable guide tubes (12 or 14) and advancing the cable 170 through the cannula 53 and exiting the cable from the near port 56 of the opposing cable guide tube (FIG. 23). Applying forces on the first and second handle extension 16,18 (FIG. 24) to cause the first and second cable guide tubes 12,14 to move away from each other while concurrently causing a restraint tip 78 of a second handle extension 18 to slide against and be released from tooth 160 of a biased rocker 30 (FIG. 25) making up releaseable hinge portion 20. Separating the pivot cup 64 of a second handle extension 18 from a handle pin 26 portion of a first handle extension 16 (FIG. 26). Then retracting a first handle tube portion 22 and a second handle tube portion 24 from the incision 178 while leaving the surgical cable 170 looped around the bone 174 (FIG. 27). Then proceeding to tighten and secure the surgical cable using one or more of a cable tensioner, a cable retensioner, a crimp or other cable locking device. Closing the wound.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A surgical cable passer instrument for passing surgical cable around a bone through a surgical incision comprising:
   a first handle tube portion;
   a second handle tube portion;
   said first handle tube portion comprising a first cable guide tube having a central axis and a first handle extension;
   said second handle tube portion comprising a second cable guide tube having a central axis and a second handle extension;
   said first and second cable guide tubes each comprising a proximal entry segment, a middle intermediate segment, and a distal arc segment having a curved profile;
   a proximal bend positioned between said intermediate segment and said proximal entry segment;
   said proximal bend diverging each said proximal entry segment away from an instrument midline in an operable configuration;
   wherein the entire central axis of said first cable guide tube and said second cable guide tube reside in a single plane;
   at least a portion of said proximal entry segment of said first cable guide tube portion fixed to a distal portion of said first handle extension;
   at least a portion of said proximal entry segment of said second cable guide tube portion fixed to a distal portion of said second handle extension;
   said first and second cable guide tube portions comprising a cannula extending between a near port at a proximal end and a far port at a distal end;
   said far port of said first cable guide tube opposed to said far port of said second cable guide tube in an operational configuration operable to passage of surgical cable therebetween though said cannula;
   said distal arc segments of said first cable guide tube and said second guide tube defining a bone aperture therebetween for passing a bone therethrough;
   and a releasable hinge portion joining said first handle tube portion and said second handle tube portion at distal ends of said first handle extension and said second handle extension.

2. The surgical cable passer instrument of claim 1 wherein in an operable configuration a central axis of said first cable guide tube and said second cable guide tube are aligned and provide for the continuous passage of a surgical cable between said near ports.

3. The surgical cable passer instrument of claim 1 wherein a pivot boss extending from a distal end of the second handle extension articulates within a pivot cavity at a distal end of the first handle extension.

4. The surgical cable passer instrument of claim 3 further comprising a first pivot finger and a second pivot finger extending from the distal end of said first handle extension and wherein a handle pin extends between said first and second pivot fingers.

5. The surgical cable passer instrument of claim 4 further comprising an open pivot cup on said pivot boss wherein said pivot cup articulates with said handle pin.

6. The surgical cable passer instrument of claim 1 further comprising a rocker wherein said rocker resides in a rocker cavity at a distal end of said first handle extension.

7. The surgical cable passer instrument of claim 6 wherein said rocker comprises a tooth at one end of said rocker and a spring pad at an opposing end of said rocker.

8. The surgical cable passer instrument of claim 7 further comprising:
   a pivot boss;
   said pivot boss extending from a distal end of a handle extension;
   wherein said tooth at one end of said rocker engages a restraint tip extending from said pivot boss in an operational mode operable to prevent unexpected separation between said first handle tube portion and said second handle tube portion.

9. The surgical cable passer instrument of claim 1 wherein said intermediate segment of said first cable guide tube and intermediate segment of said second cable guide tube are generally parallel in the operational configuration.

10. The surgical cable passer instrument of claim 1 wherein said proximal entry segment of said first cable guide tube and said proximal entry segment of said second cable guide tube diverge at a proximal end from each other in the operational configuration.

11. A surgical cable passer instrument for passing surgical cable around a bone through a surgical incision comprising:
    a first handle tube portion;
    a second handle tube portion;
    said first handle tube portion comprising a first cable guide tube having a central axis and a first handle extension;
    said second handle tube portion comprising a second cable guide tube having a central axis and a second handle extension;
    a proximal portion of said first cable guide tube portion fixed to a distal portion of said first handle extension;
    a proximal portion of said second cable guide tube portion fixed to a distal portion of said second handle extension;
    said first and second cable guide tubes comprising a cannula extending between a near port at a proximal end and a far port at a distal end;
    said first and second cable guide tube comprising an arc segment at a distal end having a curved profile;
    said far port of said first cable guide tube opposed to said far port of said second cable guide tube in an operational configuration for passage of surgical cable therebetween though said cannula;
    said arc segments of said first cable guide tube and said second guide tube defining a bone aperture therebetween for passing a bone therethrough;
    and a releasable hinge portion joining said first handle tube portion and said second handle tube portion at distal ends of said first handle extension and said second handle extension;
    and wherein movement of said first handle extension and second handle extension away from an instrument midline results in a consequent interlocking between said first handle tube portion and said second handle tube portion.

12. The surgical cable passer instrument of claim 11 wherein in an operable configuration a central axis of said first cable guide tube and said second cable guide tube are aligned and provide for the continuous passage of a surgical cable between said near ports.

13. The surgical cable passer instrument of claim 11 wherein a pivot boss extending from a distal end of the second handle extension articulates within a pivot cavity at a distal end of the first handle extension.

14. The surgical cable passer instrument of claim 13 further comprising a first pivot finger and a second pivot finger extending from the distal end of said first handle extension and wherein a handle pin extends between said first and second pivot fingers.

15. The surgical cable passer instrument of claim 14 further comprising an open pivot cup on said pivot boss wherein said pivot cup articulates with said handle pin.

16. The surgical cable passer instrument of claim 11 further comprising a rocker wherein said rocker resides in a rocker cavity at a distal end of said first handle extension.

17. The surgical cable passer instrument of claim 16 wherein said rocker comprises a tooth at one end of said rocker and a spring pad at an opposing end of said rocker.

18. The surgical cable passer instrument of claim 17 further comprising:
   a pivot boss;
   said pivot boss extending from a distal end of a handle extension;
   wherein said tooth at one end of said rocker engages a restraint tip extending from said pivot boss in an operational mode operable to prevent unexpected separation between said first handle tube portion and said second handle tube portion.

19. The surgical cable passer instrument of claim 11 wherein said first and second cable guide tubes comprise a proximal entry segment, a middle intermediate segment, and a distal arc segment wherein said intermediate segment of first cable guide tube and intermediate segment of said second cable guide tube are generally parallel in the operational configuration.

20. The surgical cable passer instrument of claim 11 wherein said first and second cable guide tubes comprise a proximal entry segment, a middle intermediate segment, and a distal arc segment wherein said proximal entry segment of said first cable guide tube and proximal entry segment of said second cable guide tube diverge at a proximal end from each other in the operational configuration.

\* \* \* \* \*